US 11,207,014 B2

(12) United States Patent
Barnes

(10) Patent No.: US 11,207,014 B2
(45) Date of Patent: Dec. 28, 2021

(54) AUTOMATIC SENSOR SELECTION

(71) Applicant: Lockheed Martin Corporation, Bethesda, MD (US)

(72) Inventor: Gavin A. Barnes, St. Cloud, FL (US)

(73) Assignee: Lockheed Martin Corporation, Bethesda, MD (US)

(*) Notice: Subject to any disclaimer, the term of this patent is extended or adjusted under 35 U.S.C. 154(b) by 137 days.

(21) Appl. No.: 16/116,048

(22) Filed: Aug. 29, 2018

(65) Prior Publication Data

US 2019/0059774 A1 Feb. 28, 2019

Related U.S. Application Data

(60) Provisional application No. 62/552,171, filed on Aug. 30, 2017.

(51) Int. Cl.
*A61B 5/316* (2021.01)
*A61F 2/72* (2006.01)
(Continued)

(52) U.S. Cl.
CPC .............. *A61B 5/316* (2021.01); *A61B 5/389* (2021.01); *A61B 5/4851* (2013.01); *A61F 2/72* (2013.01);
(Continued)

(58) Field of Classification Search
CPC ..... A61B 5/04888; A61B 5/316; A61B 5/389; A61B 5/4851; A61B 5/313;
(Continued)

(56) References Cited

U.S. PATENT DOCUMENTS 2,010,482 A 8/1935 Cobb
3,268,927 A 8/1966 Markowitz
(Continued)

FOREIGN PATENT DOCUMENTS

CN 105769185 A 7/2016
JP H03105191 U 10/1991
(Continued)

OTHER PUBLICATIONS

Non-Final Office Action for U.S. Appl. No. 15/359,806, dated Apr. 1, 2020, 12 pages.
(Continued)

*Primary Examiner* — Bruce E Snow
*Assistant Examiner* — Melissa A Hoban
(74) *Attorney, Agent, or Firm* — Withrow & Terranova, PLLC

(57) ABSTRACT

Automatic electromyography (EMG) electrode selection for robotic devices is disclosed. A plurality of signals from a corresponding plurality of sensors coupled to a skin of a user is received. For each pair of at least some pairs of the plurality of sensors, a sensor pair signature is generated based on differences in signals that are generated by the respective pair of sensors. Each of the sensor pair signatures is compared to a predetermined sensor pair signature to identify a particular pair of sensors. A signal difference between two signals generated by the particular pair of sensors is subsequently utilized to generate a command to drive a motor.

11 Claims, 3 Drawing Sheets

(51) Int. Cl.
   *A61H 3/00* (2006.01)
   *A61B 5/00* (2006.01)
   *A61B 5/389* (2021.01)
   *A61F 2/70* (2006.01)
   *A61B 5/313* (2021.01)

(52) U.S. Cl.
   CPC ............... *A61H 3/00* (2013.01); *A61B 5/313* (2021.01); *A61B 2562/046* (2013.01); *A61F 2002/704* (2013.01); *A61H 2201/5007* (2013.01); *A61H 2230/085* (2013.01)

(58) Field of Classification Search
   CPC ............... A61B 2562/046; A61F 2/72; A61F 2002/704; A61H 3/00; A61H 2230/085; A61H 2201/5007
   See application file for complete search history.

(56) References Cited

U.S. PATENT DOCUMENTS

| | | | |
|---|---|---|---|
| 3,964,182 | A | 6/1976 | Pomeret et al. |
| 4,258,556 | A | 3/1981 | Ruyten et al. |
| 5,016,869 | A | 5/1991 | Dick et al. |
| 5,020,790 | A | 6/1991 | Beard et al. |
| 5,054,476 | A | 10/1991 | Petrofsky et al. |
| 5,471,405 | A | 11/1995 | Marsh |
| 5,476,441 | A | 12/1995 | Durfee et al. |
| 5,865,426 | A | 2/1999 | Kazerooni |
| 5,954,677 | A | 9/1999 | Albrecht et al. |
| 5,993,404 | A | 11/1999 | McNiel |
| 6,039,707 | A | 3/2000 | Crawford et al. |
| 6,886,812 | B2 | 5/2005 | Kazerooni |
| 6,913,583 | B2 | 7/2005 | Jestrabek-Hart |
| 7,153,242 | B2 | 12/2006 | Goffer |
| 7,163,518 | B1 | 1/2007 | Roche et al. |
| 7,571,839 | B2 | 8/2009 | Chu et al. |
| 7,628,766 | B1 | 12/2009 | Kazerooni et al. |
| 7,883,546 | B2 | 2/2011 | Kazerooni et al. |
| 7,947,004 | B2 | 5/2011 | Kazerooni et al. |
| 8,057,410 | B2 | 11/2011 | Angold et al. |
| 8,070,700 | B2 | 12/2011 | Kazerooni et al. |
| 8,171,570 | B2 | 5/2012 | Adarraga |
| 8,231,688 | B2 | 7/2012 | Fairbanks et al. |
| 8,257,291 | B2 | 9/2012 | Kazerooni et al. |
| 8,307,572 | B2 | 11/2012 | Foxen et al. |
| 8,394,038 | B2 | 3/2013 | Ashihara et al. |
| 8,672,865 | B2 | 3/2014 | Franke et al. |
| 8,702,632 | B2 | 4/2014 | Han et al. |
| 8,801,641 | B2 | 8/2014 | Kazerooni et al. |
| 8,894,592 | B2 | 11/2014 | Amundson et al. |
| 8,945,028 | B2 | 2/2015 | Kazerooni et al. |
| 8,968,222 | B2 | 3/2015 | Kazerooni et al. |
| 9,011,354 | B2 | 4/2015 | Angold et al. |
| 9,333,644 | B2 | 5/2016 | Angold |
| 9,492,300 | B2 | 11/2016 | Bujold et al. |
| 9,662,262 | B2 | 5/2017 | Hollander et al. |
| 9,808,073 | B1 | 11/2017 | Maxwell et al. |
| 10,124,484 | B1 * | 11/2018 | Barnes .................. B25J 9/0006 |
| 10,548,800 | B1 | 2/2020 | Barnes |
| 10,561,568 | B1 | 2/2020 | Maxwell et al. |
| 2003/0062241 | A1 | 4/2003 | Irby et al. |
| 2003/0073552 | A1 | 4/2003 | Knight |
| 2003/0093018 | A1 | 5/2003 | Albrecht et al. |
| 2003/0109817 | A1 | 6/2003 | Berl |
| 2003/0115954 | A1 | 6/2003 | Zemlyakov et al. |
| 2004/0106881 | A1 * | 6/2004 | McBean .................. A61F 2/72 601/5 |
| 2004/0237351 | A1 | 12/2004 | Howell |
| 2005/0137717 | A1 | 6/2005 | Gramnas et al. |
| 2006/0064047 | A1 | 3/2006 | Shimada et al. |
| 2006/0107433 | A1 | 5/2006 | Olson |
| 2006/0260620 | A1 | 11/2006 | Kazerooni et al. |
| 2007/0056592 | A1 | 3/2007 | Angold et al. |
| 2007/0123997 | A1 | 5/2007 | Herr et al. |
| 2007/0233279 | A1 | 10/2007 | Kazerooni et al. |
| 2008/0009771 | A1 | 1/2008 | Perry et al. |
| 2008/0234608 | A1 | 9/2008 | Sankai |
| 2009/0210093 | A1 | 8/2009 | Jacobsen et al. |
| 2009/0292369 | A1 | 11/2009 | Kazerooni et al. |
| 2009/0326406 | A1 | 12/2009 | Tan et al. |
| 2010/0076360 | A1 | 3/2010 | Shimada et al. |
| 2010/0094185 | A1 | 4/2010 | Amundson et al. |
| 2010/0152630 | A1 | 6/2010 | Matsuoka et al. |
| 2010/0210980 | A1 | 8/2010 | Kudoh |
| 2010/0254696 | A1 | 10/2010 | McKay |
| 2010/0324699 | A1 | 12/2010 | Herr et al. |
| 2011/0040216 | A1 | 2/2011 | Herr et al. |
| 2011/0105966 | A1 | 5/2011 | Kazerooni et al. |
| 2011/0166489 | A1 | 7/2011 | Angold et al. |
| 2011/0201978 | A1 | 8/2011 | Jeon et al. |
| 2011/0214524 | A1 | 9/2011 | Jacobsen et al. |
| 2011/0264014 | A1 | 10/2011 | Angold |
| 2011/0266323 | A1 | 11/2011 | Kazerooni et al. |
| 2012/0004736 | A1 | 1/2012 | Goldfarb et al. |
| 2012/0073165 | A1 | 3/2012 | McKeown |
| 2012/0172770 | A1 | 7/2012 | Almesfer et al. |
| 2012/0192461 | A1 | 8/2012 | Backus |
| 2012/0283845 | A1 | 11/2012 | Herr et al. |
| 2012/0292361 | A1 | 11/2012 | Thiruppathi |
| 2013/0023800 | A1 | 1/2013 | Bédard et al. |
| 2013/0102935 | A1 | 4/2013 | Kazerooni et al. |
| 2013/0150980 | A1 | 6/2013 | Swift et al. |
| 2013/0197408 | A1 | 8/2013 | Goldfarb et al. |
| 2013/0226048 | A1 | 8/2013 | Unluhisarcikli et al. |
| 2013/0231595 | A1 | 9/2013 | Zoss et al. |
| 2013/0237884 | A1 | 9/2013 | Kazerooni et al. |
| 2013/0296746 | A1 | 11/2013 | Herr et al. |
| 2013/0303950 | A1 | 11/2013 | Angold et al. |
| 2013/0317648 | A1 | 11/2013 | Assad |
| 2013/0331744 | A1 | 12/2013 | Kamon |
| 2014/0001222 | A1 | 1/2014 | Vierthaler et al. |
| 2014/0046234 | A1 | 2/2014 | DeSousa |
| 2014/0094729 | A1 | 4/2014 | Lachance et al. |
| 2014/0200491 | A1 | 7/2014 | Julin et al. |
| 2014/0207017 | A1 | 7/2014 | Gilmore et al. |
| 2014/0276264 | A1 | 9/2014 | Caires et al. |
| 2014/0330431 | A1 | 11/2014 | Hollander et al. |
| 2014/0358053 | A1 | 12/2014 | Triolo et al. |
| 2015/0001269 | A1 | 1/2015 | Sacksteder |
| 2015/0057984 | A1 * | 2/2015 | Nicoletti ............ A61B 5/04001 703/2 |
| 2015/0081036 | A1 | 3/2015 | Nakanishi et al. |
| 2015/0134080 | A1 | 5/2015 | Roh |
| 2015/0173918 | A1 * | 6/2015 | Herr .................... A61N 1/36003 623/25 |
| 2015/0173992 | A1 | 6/2015 | Wang |
| 2015/0272501 | A1 | 10/2015 | Maceachern et al. |
| 2015/0272809 | A1 | 10/2015 | Accoto et al. |
| 2015/0313786 | A1 | 11/2015 | Sano |
| 2015/0321340 | A1 | 11/2015 | Smith |
| 2015/0366694 | A1 | 12/2015 | Bujold et al. |
| 2016/0015589 | A1 | 1/2016 | Lee et al. |
| 2016/0016307 | A1 | 1/2016 | Choi et al. |
| 2016/0038313 | A1 | 2/2016 | Kim et al. |
| 2016/0038371 | A1 | 2/2016 | Sandler et al. |
| 2016/0058647 | A1 | 3/2016 | Maddry |
| 2016/0067550 | A1 | 3/2016 | Breach et al. |
| 2016/0158033 | A1 | 6/2016 | Hahn et al. |
| 2016/0184165 | A1 | 6/2016 | Ohta et al. |
| 2016/0262969 | A1 | 9/2016 | Ohta et al. |
| 2017/0014297 | A1 | 1/2017 | Grygorowicz et al. |
| 2017/0014993 | A1 | 1/2017 | Barnes |
| 2017/0061828 | A1 | 3/2017 | Artemiadis et al. |
| 2017/0181917 | A1 | 6/2017 | Ohta et al. |
| 2017/0246740 | A1 | 8/2017 | Barnes |
| 2017/0303849 | A1 | 10/2017 | De Sapio et al. |
| 2017/0340504 | A1 | 11/2017 | Sanz Merodio et al. |
| 2019/0021883 | A1 * | 1/2019 | Herr ..................... A61F 2/80 |

FOREIGN PATENT DOCUMENTS

| | | |
|---|---|---|
| JP | 3024978 U | 6/1996 |
| JP | 2003104682 A | 4/2003 |

(56) References Cited

FOREIGN PATENT DOCUMENTS

| | | |
|---|---|---|
| JP | 200911818 A | 1/2009 |
| KR | 101570679 B1 | 11/2015 |
| WO | 2012154580 A1 | 11/2012 |
| WO | 2013116900 A1 | 8/2013 |
| WO | 2014125387 A2 | 8/2014 |
| WO | 2014159608 A1 | 10/2014 |
| WO | WO 2015/087164 A1 * | 6/2015 |
| WO | 2016029159 A2 | 2/2016 |
| WO | 2017025363 A1 | 2/2017 |
| WO | 2017137930 A1 | 8/2017 |

OTHER PUBLICATIONS

Office Action for Canadian Patent Application No. 3,063,399, dated Feb. 28, 2020, 3 pages.
Notice of Reasons for Refusal for Japanese Patent Application No. 2018-502176, dated Mar. 3, 2020, 10 pages.
International Preliminary Report on Patentability for International Patent Application No. PCT/US2018/048517, dated Mar. 12, 2020, 10 pages.
Non-Final Office Action for U.S. Appl. No. 15/597,213, dated Apr. 30, 2019, 10 pages.
Interview Summary for U.S. Appl. No. 15/181,934, dated Apr. 12, 2019, 11 pages.
Non-Final Office Action for U.S. Appl. No. 14/744,855, dated Apr. 25, 2019, 9 pages.
Written Opinion for Singaporean Patent Application No. 11201800019U, dated Mar. 12, 2019, 7 pages.
Final Office Action for U.S. Appl. No. 15/359,806, dated May 31, 2019, 14 pages.
Advisory Action and AFCP 2.0 Decision for U.S. Appl. No. 15/181,934, dated Jan. 9, 2019, 4 pages.
Non-Final Office Action for U.S. Appl. No. 15/181,934, dated Feb. 26, 2019, 23 pages.
Partial Supplementary European Search Report for European Patent Application No. 16828290.3, dated Mar. 1, 2019, 12 pages.
International Search Report and Written Opinion for International Patent Application No. PCT/US2018/048517, dated Dec. 31, 2018, 13 pages.
Whitwam, Ryan, et al., "Banks now have money-grabbing robotic exoskeletons that are probably helpful for robbing banks," PCMag Digital Group, May 9, 2015, Ziff Davis, LLC, www.geek.com/?s=japanese+banks+now+have+money+grabbing&x=0&y=0, 4 pages.
Non-Final Office Action for U.S. Appl. No. 13/084,265, dated Sep. 10, 2015, 7 pages.
Extended European Search Report for European Patent Application No. 11766862.4, dated May 27, 2014, 4 pages.
Notice of Reasons for Refusal for Japanese Patent Application No. 2013-504019, dated Feb. 24, 2015, 6 pages.
International Search Report for PCT/US2011/031956, dated Jun. 21, 2011, 2 pages.
International Preliminary Report on Patentability for PCT/US2011/031956, dated Oct. 9, 2012, 6 pages.
Supplemental Notice of Allowability for U.S. Appl. No. 13/084,265, dated Jan. 25, 2016, 3 pages.
Notice of Reasons for Refusal for Japanese Patent Application No. 2013-504019, dated Dec. 22, 2015, 6 pages.
Decision to Grant for Japanese Patent Application No. 2013-504019, dated Aug. 16, 2016, 6 pages.
International Search Report and Written Opinion for International Patent Application No. PCT/US2016/042427, dated Oct. 24, 2016, 18 pages.
Artemiadis, Panagiotis K. et al., "EMG-based Position and Force Estimates in Coupled Human-Robot Systems: Towards EMG-controlled Exoskeletons," Experimental Robotics: The Eleventh International Symposium (book), vol. 54, 2009, Springer Berlin Heidelberg, pp. 1-10.

Ferris, Daniel P. et al., "An Ankle-Foot Orthosis Powered by Artificial Muscles," Journal of Applied Biomechanics, vol. 21, Issue 2, May 2005, Human Kinetics, Inc., 3 pages.
Ferris, Dan et al., "An Improved Ankle-Foot Orthosis Powered by Artificial Pneumatic Muscles," XIXth Congress of the International Society of Biomechanics: the human body in motion, Jul. 6-11, 2003, Dunedin, New Zealand, University of Otago, 17 pages.
Ferris, Daniel P. et al., "Development of a myoelectrically controlled lower limb orthosis for human locomotion," Proceedings of the NCMRR Symposium "Medical Rehab on the Move: Spotlight on BioEngineering," Abstract, Jan. 4-5, 2001, Bethesda, Maryland, Supported by NIH AR08602 and U.S. Dept. of Veterans Affairs Center Grant #A0806C, 2 pages.
Gordon, Keith E. et al., "Motor Adaptation During Walking with a Powered Ankle Foot Orthosis," Journal of NeuroEngineering and Rehabilitation, vol. 4, 2007, BioMed Central Ltd, 2 pages.
Kawamoto, Hiroaki et al., "Power Assist Method for HAL-3 using EMG-based Feedback Controller," IEEE International Conference on Systems, Man and Cybernetics, Oct. 8, 2003, IEEE, pp. 1648-1653.
Sawicki, Gregory S. et al., "A Knee-Ankle-Foot Orthosis (KAFO) Powered by Artificial Pneumatic Muscles," XIXth Congress of the International Society of Biomechanics: the human body in motion, Jul. 6-11, 2003, Dunedin, New Zealand, 1 page.
Sawicki, Gregory S. et al., "Mechanics and energetics of level walking with powered ankle exoskeletons," The Journal of Experimental Biology, vol. 211, Feb. 19, 2009, The Company of Biologists, pp. 1402-1413.
Non-Final Office Action and Examiner-Initiated Interview Summary for U.S. Appl. No. 14/744,892, dated Feb. 17, 2017, 44 pages.
Notice of Allowance and Notice Requiring Inventor's Oath or Declaration for U.S. Appl. No. 14/744,892, dated Jul. 5, 2017, 11 pages.
Corrected Notice of Allowance for U.S. Appl. No. 14/744,892, dated Jul. 14, 2017, 7 pages.
Non-Final Office Action for U.S. Appl. No. 15/181,934, dated Mar. 27, 2018, 17 pages.
Non-Final Office Action for U.S. Appl. No. 14/801,941, dated Apr. 25, 2018, 9 pages.
Notice of Allowance for U.S. Appl. No. 14/801,941, dated Sep. 19, 2018, 8 pages.
Notice of Allowance for U.S. Appl. No. 15/371,709, dated Jul. 13, 2018, 10 pages.
International Preliminary Report on Patentability for PCT/US2016/042427, dated Jan. 23, 2018, 13 pages.
International Search Report and Written Opinion for International Patent Application No. PCT/US2018/032940, dated Sep. 12, 2018, 17 pages.
Final Office Action for U.S. Appl. No. 15/181,934, dated Oct. 31, 2018, 22 pages.
Non-Final Office Action for U.S. Appl. No. 15/359,806, dated Nov. 16, 2018, 12 pages.
Extended European Search Report for European Patent Application No. 18801352.8, dated May 28, 2020, 7 pages.
Applicant-Initiated Interview Summary for U.S. Appl. No. 15/359,806, dated Jun. 23, 2020, 6 pages.
Author Unknown, "Definition of avoid," Merriam-Webster Dictionary, 2019, accessed online from https://www.merriam-webster.com/dictionary/avoid, Merriam-Webster, Inc., 4 pages.
Notice of Allowance for U.S. Appl. No. 15/597,213, dated Aug. 15, 2019, 7 pages.
Notice of Allowance and Examiner-Initiated Interview Summary for U.S. Appl. No. 15/181,934, dated Jul. 16, 2019, 17 pages.
Final Office Action for U.S. Appl. No. 14/744,855, dated Aug. 13, 2019, 9 pages.
Extended European Search Report for European Patent Application No. 16828290.3, dated Aug. 14, 2019, 11 pages.
Notice of Allowance and AFCP 2.0 Decision for U.S. Appl. No. 14/744,855, dated Oct. 9, 2019, 9 pages.
Examination Report No. 2 for Australian Patent Application No. 2016296482, dated Feb. 16, 2021, 4 pages.
Notice of Allowance for U.S. Appl. No. 15/359,806, dated Oct. 5, 2020, 7 pages.

(56) References Cited

OTHER PUBLICATIONS

Examination Report No. 1 for Australian Patent Application No. 2016296482, dated Sep. 21, 2020, 6 pages.
Decision to Grant for Japanese Patent Application No. 2018-502176, dated Sep. 8, 2020, 6 pages.
Fleischer, Christian, et al., "Torque Control of an Exoskeletal Knee With EMG Signals," Proceedings of the Joint Conference on Robotics, May 2006, Munich, Germany, VDI, 9 pages.
International Search Report and Written Opinion for International Patent Application No. PCT/US2019/024293, dated Jul. 4, 2019, 13 pages.
International Preliminary Report on Patentability for International Patent Application No. PCT/US2019/024293, dated Oct. 8, 2020, 9 pages.
Extended European Search Report for European Patent Application No. 18850130.8, dated Mar. 31, 2021, 10 pages.
Notice of Acceptance for Australian Patent Application No. 2016296482, dated Jul. 26, 2021, 3 pages.
Examination Report for European Patent Application No. 16828290.3, dated Jul. 23, 2021, 4 pages.
Office Action for Canadian Patent Application No. 2,991,636, dated Aug. 20, 2021, 4 pages.

* cited by examiner

AUTOMATIC SENSOR SELECTION

RELATED APPLICATION

This application claims the benefit of U.S. Provisional Application No. 62/552,171, filed on Aug. 30, 2017, entitled "AUTOMATIC EMG ELECTRODE SELECTION FOR ROBOTIC DEVICES," the disclosure of which is hereby incorporated herein by reference in its entirety.

TECHNICAL FIELD

The embodiments relate generally to the use of sensors (i.e. electrodes) in conjunction with devices, such as prosthetics and exoskeletons, and, in particular, to automatic sensor selection.

BACKGROUND

The use of electromyography (EMG) in robotic devices, such as prosthetics and exoskeletons, requires proper placement of EMG sensors on a user's skin over the relevant muscle groups. Proper placement requires knowledge of muscle anatomy, or a skilled physiologist, neither of which may be available at the time such a robotic device will be used.

Accordingly, robotic devices could be more widely used if EMGs could be properly placed on an individual by someone with little to no knowledge of physiology.

SUMMARY

The embodiments implement automatic electromyography (EMG) sensor selection for use in robotic devices. The embodiments, among other advantages, eliminate a need to precisely place a pair of EMG sensors on a skin of a user. While the embodiments will be discussed herein in the context of an exoskeleton, the embodiments have applicability in any application where EMG sensor signals are used to drive a motor in conjunction with the movements of a user. For example, the embodiments also have applicability in the use of motorized prosthetics.

In one embodiment a method is provided. The method includes receiving, by a computing device comprising a processor device, a plurality of signals from a corresponding plurality of sensors coupled to a skin of a user, the plurality of sensors comprising at least three sensors. The method further includes, for each respective pair of sensors of a plurality of pairs of sensors of the plurality of sensors, generating a corresponding sensor pair signature based on differences in signals that are generated by the respective pair of sensors. The method further includes comparing each of the sensor pair signatures to a predetermined sensor pair signature to identify a particular pair of sensors, and subsequently utilizing a signal difference between two signals generated by the particular pair of sensors to generate a command to drive a motor.

In another embodiment a system is provided. The system includes an electromyography (EMG) sensor assembly comprising at least three EMG sensors configured to be coupled to a skin of a user. The system further includes a processor device coupled to the EMG sensor assembly. The processor device is configured to receive a plurality of signals from the at least three EMG sensors. The processor device is further configured to, for each respective pair of EMG sensors of a plurality of pairs of EMG sensors of the at least three EMG sensors, generate a corresponding sensor pair signature based on differences in signals that are generated by the respective pair of EMG sensors. The processor device is further configured to compare each of the sensor pair signatures to a predetermined sensor pair signature to identify a particular pair of EMG sensors, and subsequently utilize a signal difference between two signals generated by the particular pair of EMG sensors to generate a command to drive a motor.

In another embodiment another method is provided. The method includes receiving a plurality of signals from a corresponding plurality of sensors coupled to a skin of a user. The method further includes based on the plurality of signals and a predetermined signal signature, selecting at least one sensor, and subsequently utilizing a signal generated by the at least one sensor to generate a command to drive a motor.

Those skilled in the art will appreciate the scope of the disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Any flowcharts discussed herein are necessarily discussed in some sequence for purposes of illustration, but unless otherwise explicitly indicated, the embodiments are not limited to any particular sequence of steps. The use herein of ordinals in conjunction with an element is solely for distinguishing what might otherwise be similar or identical labels, such as "first format" and "second format," and does not imply a priority, a type, an importance, or other attribute, unless otherwise stated herein. The term "about" used herein in conjunction with a numeric value means any value that is within a range of ten percent greater than or ten percent less than the numeric value.

The use of electromyography (EMG) in robotic devices, such as prosthetics and exoskeletons, requires proper placement of EMG sensors on a user's skin over the relevant muscle groups. Proper placement requires knowledge of muscle anatomy, or a skilled physiologist, neither of which may be available at the time a robotic device will be used.

The embodiments implement automatic EMG sensor selection for use in robotic devices that eliminates a need to precisely place a pair of EMG sensors on a skin of a user. While the embodiments will be discussed herein in the context of an exoskeleton, the embodiments have applicability in any application where EMG sensor signals are used to drive a motor in conjunction with the movements of a user. For example, the embodiments also have applicability in the use of motorized prosthetics.

Figure 1:
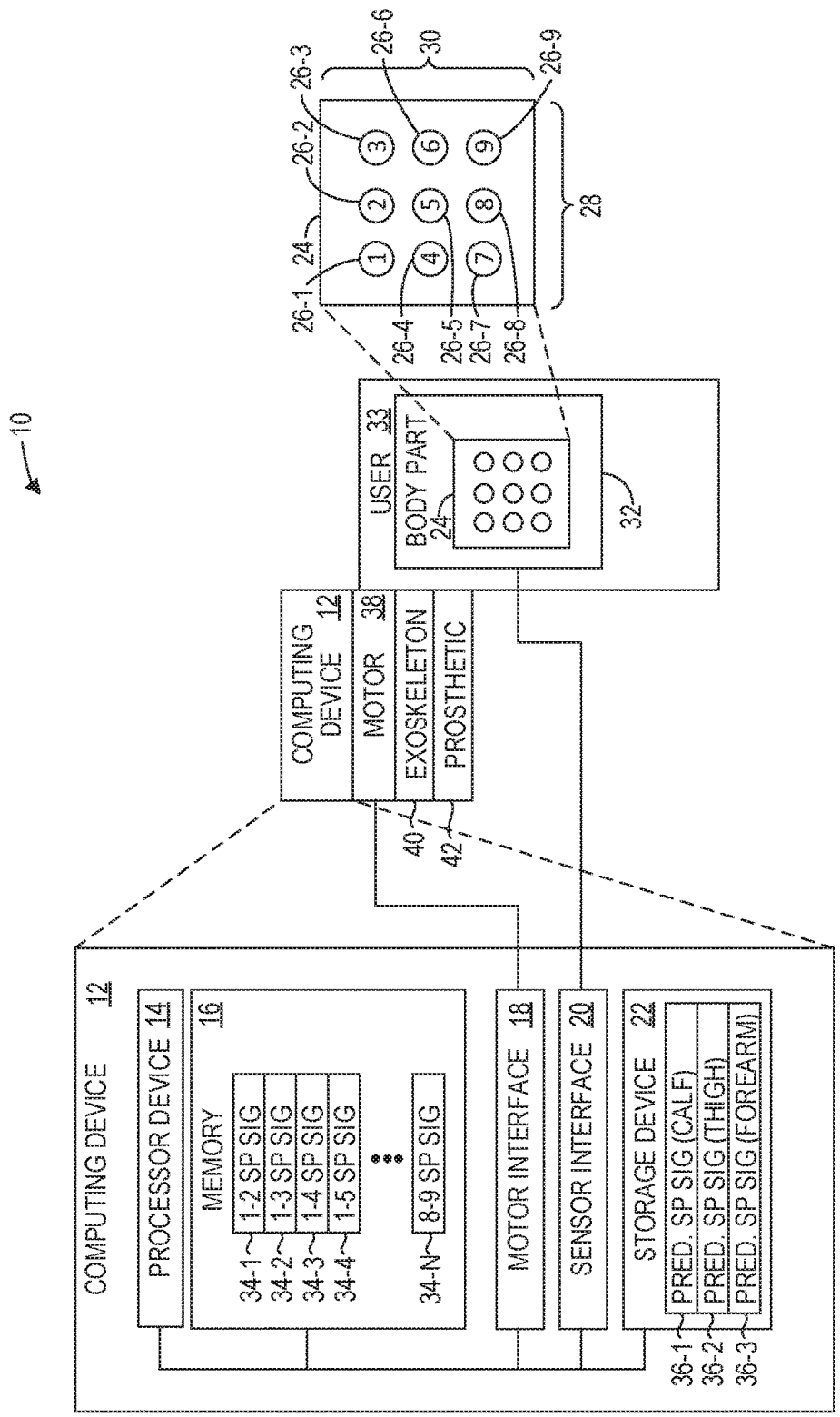
FIG. 1 is a block diagram of an environment in which embodiments can be practiced.

FIG. 1 is a block diagram of an environment 10 in which embodiments can be practiced. The environment 10 includes a computing device 12. The computing device 12 includes a processor device 14 that is communicatively coupled to a memory 16, a motor interface 18, a sensor interface 20 and a storage device 22. The sensor interface 20 is communicatively coupled to an EMG sensor assembly 24. The EMG sensor assembly 24 comprises a plurality of EMG sensors 26-1-26-9 (generally, EMG sensors 26). In this example, there are nine EMG sensors 26 arranged in a grid, although the embodiments are not limited to any particular pattern or number of EMG sensors 26. The EMG sensor assembly 24, in this embodiment, may have a width 28 and an equal height 30 of, for example, 2 inches to 4 inches. The EMG sensor assembly 24 may include a flexible and adhesive substrate to which the EMG sensors 26 are fixed, facilitating coupling of the EMG sensor assembly 24 to a skin over a desired muscle group of a body part 32 of a user 33. The body part 32 may comprise any suitable part of the body, such as, by way of non-limiting example, a calf of the user 33, a thigh of the user 33, a forearm of the user 33, or the like.

Each of the EMG sensors 26 generates a signal that is received by the processor device 14. The processor device 14 may communicate with the EMG sensor assembly 24 wirelessly or via a wired connection. The processor device 14 determines the different combinations of pairs of EMG sensors 26 in the EMG sensor assembly 24. As an example, one pair of EMG sensors 26 includes the EMG sensor 26-1 and the EMG sensor 26-2; another pair of EMG sensors 26 includes the EMG sensor 26-1 and the EMG sensor 26-3; and another pair of EMG sensors 26 includes the EMG sensor 26-1 and the EMG sensor 26-4. In total, for nine EMG sensors 26, the processor device 14 may determine that thirty-six different pairs of EMG sensors 26 exist.

For each pair of EMG sensors 26, the processor device 14 generates a difference signal, sometimes referred to herein as a sensor pair signature, based on a difference between signals received by the EMG sensors 26 in the respective pair. As an example, for the pair of EMG sensors 26-1 and 26-2, the processor device 14 generates a sensor pair signature 34-1; for the pair of EMG sensors 26-1 and 26-3, the processor device 14 generates a sensor pair signature 34-2; for the pair of EMG sensors 26-1 and 26-4, the processor device 14 generates a sensor pair signature 34-3; for the pair of EMG sensors 26-1 and 26-4, the processor device 14 generates a sensor pair signature 34-4; and for the pair of EMG sensors 26-8 and 26-9, the processor device 14 generates a sensor pair signature 34-N.

Because a pair of EMG sensors 26 is sensitive to both the magnitude and orientation of the pair of EMG sensors 26 relative to the desired muscle, a difference signal generated between the same two respective EMG sensors 26 will have the opposite sign. For example, the difference signal between the pair of EMG sensors 26-1 and 26-2 will have the opposite sign from the difference signal between the pair of EMG sensors 26-2 and 26-1. Thus, in this example, with nine EMG sensors 26, the processor device 14 identifies a total of seventy two different sensor pair signatures 34. In one embodiment, the difference signal is generated by subtracting a recorded voltage of a first EMG sensor 26 from a recorded voltage of a second EMG sensor 26 of a pair of EMG sensors 26.

The storage device 22 contains one or more predetermined sensor pair signatures 36-1-36-N (generally, predetermined sensor pair signatures 36). Each predetermined sensor pair signature 36 corresponds to a particular body part of the user 33. The predetermined sensor pair signatures 36 contain a sensor pair signature against which the sensor pair signatures 34 are compared in order to select one of the sensor pair signatures 34 for use. In particular, the processor device 14 compares each sensor pair signature 34 against the predetermined sensor pair signature 36 that corresponds to the relevant body part, and selects a particular sensor pair signature 34 that is a closest match to the predetermined sensor pair signature 36.

The predetermined sensor pair signatures 36 may be generated in any of a number of different ways. In one embodiment, prior to the application of the EMG sensor assembly 24 to the user 33, an individual trained in EMG sensor placement places two EMG sensors at appropriate locations on the skin of an individual. The individual then performs one or more predetermined activities. While the individual is performing the one or more predetermined activities, the signals generated by the two EMG sensors are recorded. A predetermined sensor pair signature 36 may be generated based on the recorded sensor signals. In some embodiments, this process may be repeated with a group of individuals, and the predetermined sensor pair signature may be based on signatures generated from each of the individuals, such as via an averaging or other suitable process. In some embodiments, this process may be performed using the actual individual, in this example the user 33, to whom the EMG sensor assembly 24 will be later applied.

After the EMG sensor assembly 24 is applied to the body part 32 of the user 33, the user 33 may be requested to perform the same one or more predetermined activities used to generate the corresponding predetermined sensor pair signature 36. As an example, if the EMG sensor assembly 24 is applied to the thigh area of the user 33, the user 33 may be asked to perform a walking activity, a jogging activity, and a squat activity. While the user 33 is performing such activities, the processor device 14 generates the sensor pair signatures 34. The processor device 14 then compares the sensor pair signatures 34 to the predetermined sensor pair signature 36-2 (for the thigh body part 32 in this example) and selects a particular sensor pair signature 34 based on a closest match algorithm.

The processor device 14 subsequently utilizes the two EMG sensors 26 that correspond to the selected sensor pair signature 34 to subsequently generate commands to drive a motor 38 via the motor interface 18. The motor interface 18 may comprise, for example, a communications path, wired or wireless, and any suitable firmware and/or software used to translate commands from the processor device 14 to corresponding signals to the motor 38. The motor 38 may be any suitable motor used to drive any suitable robotic device. In one embodiment, the motor 38 comprises an exoskeleton motor used to move an exoskeleton 40. In another embodiment, the motor 38 comprises a prosthetic motor used to move a prosthetic 42. As an example, the processor device 14 may receive signals from the two EMG sensors 26 that identify the beginning of a muscle contraction of the user 33 that would result in the movement of a limb of the user 33 and, in response to such signals, generate a command to move an exoskeleton link that is coupled to the limb of the user 33 that would be moved in response to the muscle contraction. The processor device 14 may disregard any other signals received from the EMG sensors 26 other than the selected pair of EMG sensors 26.

Figure 2:
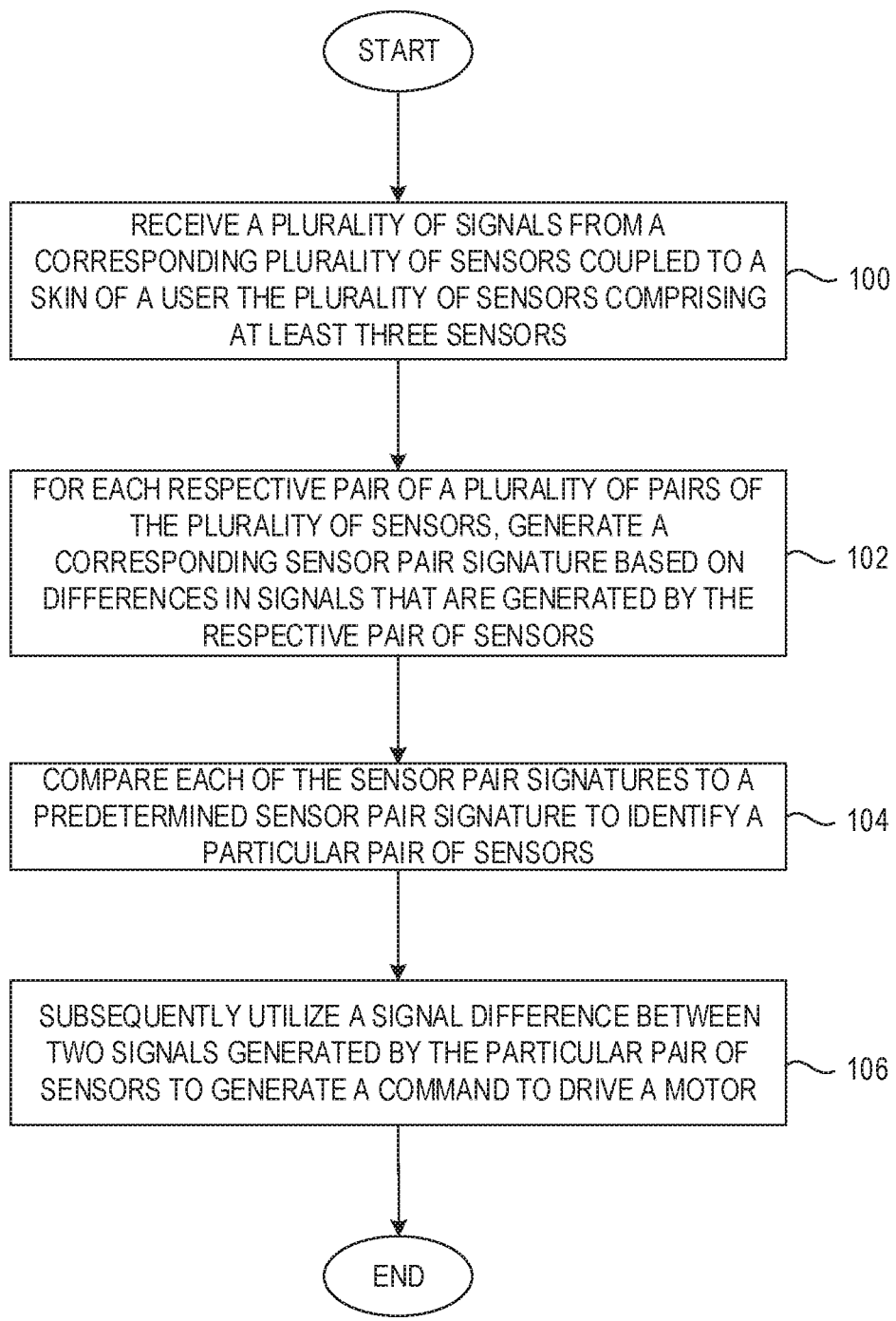
FIG. 2 is a flowchart of a method for automatic electromyography (EMG) sensor selection according to one embodiment.

FIG. 2 is a flowchart of a method for automatic EMG sensor selection according to one embodiment. FIG. 2 will be discussed in conjunction with FIG. 1. Initially, the EMG sensor assembly 24, which comprises at least three EMG sensors 26, is placed on the skin of the body part 32 of the user 33 over a desired muscle group, such as a thigh muscle, a calf muscle, or the like. In this example it will be assumed that the EMG sensor assembly 24 is placed over a thigh muscle group. The processor device 14 receives a plurality of signals from the corresponding plurality of EMG sensors 26 of the EMG sensor assembly 24 (FIG. 2, block 100). In particular, for each EMG sensor 26 in the EMG sensor assembly 24, the processor device 14 receives a separate signal. The processor device 14 determines the different combinations of pairs of EMG sensors 26 in the EMG sensor assembly 24. For each pair of at least some pairs of the plurality of EMG sensors 26, the processor device 14 generates a sensor pair signature 34 based on the differences in signals that are generated by the corresponding pair of EMG sensors 26 (FIG. 2, block 102). During this step, the user may be performing a known calibration movement, such as walking, squatting, or the like. This process may be referred to as a calibration step.

The processor device 14 compares each of the sensor pair signatures 34 to the predetermined sensor pair signature 36-2 (FIG. 1) to identify at least one pair of EMG sensors 26 (FIG. 2, block 104). The predetermined sensor pair signature 36-2 is a sensor pair signature that represents an ideal signal difference for a human performing the known calibration movement, and may be generated, for example, as discussed above. The comparison step may involve, for example, determining which pair of EMG sensors 26 generates a signal difference that most closely matches the predetermined sensor pair signature 26-2.

The processor device 14 stores identifiers of the at least one pair of EMG sensors 26 to use for subsequent operation of the motor 38. The processor device 14 subsequently utilizes a signal difference between the two signals generated by the at least one pair of EMG sensors 26 to generate a command to drive the motor 38 to move, for example, the exoskeleton 40 or prosthetic 42 (FIG. 2, block 106). For example, based on the signal difference between the two signals generated by the at least one pair of EMG sensors 26, the processor device 14 may generate a torque command that directs the motor 38 to apply a particular torque to a limb of the exoskeleton 40.

Figure 3:
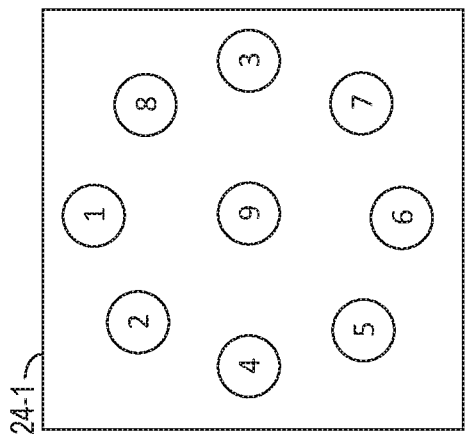
FIG. 3 is a block diagram of an EMG sensor assembly according to another embodiment.

FIG. 3 is a block diagram of an EMG sensor assembly 24-1 according to another embodiment. Other than the difference in pattern, the EMG sensor assembly 24-1 operates substantially similarly to the EMG sensor assembly 24 discussed above.

While the embodiments have been discussed in the context of pairs of EMG sensors, the embodiments have applicability with other numbers of EMG sensors, such as a single EMG sensor, or groups of EMG sensors greater than two, such as a set of three EMG sensors, four EMG sensors, or any other size set of EMG sensors. In the context of a single EMG sensor, the embodiments receive a plurality of signals from a corresponding plurality of sensors coupled to a skin of a user, based on the plurality of signals and a predetermined signal signature, select at least one sensor, and subsequently utilize a signal generated by the at least one sensor to generate a command to drive a motor.

While the embodiments have been discussed in the context of EMG sensors as examples, the embodiments are not limited to EMG sensors and have applicability to any types of sensors that require some knowledge of placement.

Those skilled in the art will recognize improvements and modifications to the preferred embodiments of the disclosure. All such improvements and modifications are considered within the scope of the concepts disclosed herein and the claims that follow.

What is claimed is:

1. A method comprising:
receiving, by a computing device comprising a processor device, a plurality of signals from a corresponding plurality of sensors coupled to a skin of a user, the plurality of sensors comprising at least three sensors including a plurality of pairs of sensors between each of the at least three sensors and each other of the at least three sensors;
for each respective pair of sensors of the plurality of pairs of sensors of the plurality of sensors, generating a corresponding sensor pair signature based on differences in signals that are generated by the respective pair of sensors;
comparing each of the sensor pair signatures to a predetermined sensor pair signature to identify a particular pair of sensors of the plurality of pairs of sensors, the predetermined sensor pair signature corresponding to a body part; and
subsequently utilizing a signal difference between two signals generated by the particular pair of sensors to generate a command to drive a motor.

2. The method of claim 1 wherein the motor comprises an exoskeleton motor coupled to an exoskeleton, and wherein subsequently utilizing the signal difference between the two signals generated by the particular pair of sensors to generate the command to drive the motor comprises:
subsequently utilizing the signal difference between the two signals generated by the particular pair of sensors to generate the command to drive the exoskeleton motor to move the exoskeleton.

3. The method of claim 1 wherein the motor comprises a prosthetic motor coupled to a prosthetic, and wherein subsequently utilizing the signal difference generated between the two signals generated by the particular pair of sensors to generate the command to drive the motor comprises:
subsequently utilizing the signal difference between the two signals generated by the particular pair of sensors to generate the command to drive the prosthetic motor to move the prosthetic.

4. The method of claim 1 wherein the plurality of sensors is fixed to an adhesive substrate, and further comprising:
placing the adhesive substrate on the skin of a body part of the user.

5. The method of claim 1 wherein the plurality of sensors is fixed to an adhesive substrate and has a dimension of less than about 3 inches by 3 inches.

6. The method of claim 1 wherein generating the sensor pair signature based on the differences in the signals that are generated by the respective pair of sensors further comprises:
for each different pair of sensors of the plurality of sensors, generating the sensor pair signature based on a difference in a voltage signal generated by each sensor of the respective pair of sensors.

7. The method of claim 1 further comprising:
after comparing each of the sensor pair signatures to the predetermined sensor pair signature to identify the particular pair of sensors, disregarding signals generated by each sensor of the plurality of sensors other than the sensors in the particular pair of sensors.

8. The method of claim 1 wherein receiving the plurality of signals from the corresponding plurality of sensors coupled to the skin of the user comprises receiving the plurality of signals from the corresponding plurality of sensors coupled to the skin of the user during a period of time the user is performing a predetermined activity.

9. The method of claim 1 further comprising:
maintaining a plurality of predetermined sensor pair signatures, each predetermined sensor pair signature corresponding to a different body part of a plurality of body parts of a user, and wherein comparing each of the sensor pair signatures to the predetermined sensor pair signature to identify the particular pair of sensors comprises comparing each of the sensor pair signatures to the predetermined sensor pair signature that corresponds to a body part on which the plurality of sensors is attached to identify the particular pair of sensors.

10. The method of claim 1, wherein the plurality of sensors is fixed to a common adhesive substrate configured to couple the plurality of sensors over the body part, and further comprising:
after identifying the particular pair of sensors, generating commands to drive the motor based on signals generated by sensors of the particular pair of sensors and disregarding signals generated by each sensor of the plurality of sensors other than the sensors of the particular pair of sensors.

11. The method of claim 1, wherein each of the plurality of sensors comprises an electromyography (EMG) sensor, and the motor comprises an exoskeleton motor coupled to an exoskeleton.

* * * * *